US010388408B2

(12) United States Patent
Osorio et al.

(10) Patent No.: US 10,388,408 B2
(45) Date of Patent: Aug. 20, 2019

(54) METHODS AND SYSTEMS FOR SECURE TRANSMISSION AND RECEPTION OF DATA BETWEEN A MOBILE DEVICE AND A CENTRAL COMPUTER SYSTEM

(71) Applicant: MD Cloud Practice Solutions, L.L.C., Dallas, TX (US)

(72) Inventors: Federico Osorio, Dallas, TX (US); Andres Gutierrez Ovalles, Dallas, TX (US)

(73) Assignee: MD Cloud Practice Solutions, L.L.C., Dallas, TX (US)

( * ) Notice: Subject to any disclaimer, the term of this patent is extended or adjusted under 35 U.S.C. 154(b) by 747 days.

(21) Appl. No.: 14/879,248

(22) Filed: Oct. 9, 2015

(65) Prior Publication Data

US 2016/0103782 A1    Apr. 14, 2016

Related U.S. Application Data

(60) Provisional application No. 62/062,601, filed on Oct. 10, 2014.

(51) Int. Cl.
| G06F 13/00 | (2006.01) |
|---|---|
| G16H 10/60 | (2018.01) |
| H04L 29/08 | (2006.01) |
| H04W 12/06 | (2009.01) |
| G06F 19/00 | (2018.01) |
| G06F 21/60 | (2013.01) |
| H04W 12/02 | (2009.01) |
| G06F 21/62 | (2013.01) |
| H04L 29/06 | (2006.01) |

(52) U.S. Cl.
CPC ............ *G16H 10/60* (2018.01); *G06F 19/328* (2013.01); *G06F 21/606* (2013.01); *G06F 21/6245* (2013.01); *H04L 67/143* (2013.01); *H04W 12/02* (2013.01); *H04W 12/06* (2013.01); *H04L 63/0428* (2013.01)

(58) Field of Classification Search
CPC .... G06F 19/322; G06F 19/328; G06F 21/606; G06F 21/6245; H04W 12/02; H04W 12/06; G16H 10/60; H04L 67/143; H04L 63/0428; H04L 63/08; H04L 9/0894; H04L 2209/80; H04L 2209/88
USPC ................... 709/227, 228, 220–222; 726/26; 713/165, 193
See application file for complete search history.

(56) References Cited

U.S. PATENT DOCUMENTS

| 3,916,095 A | 10/1975 | Weber et al. |
|---|---|---|
| 5,671,246 A | 9/1997 | McIntyre |
| 6,128,621 A * | 10/2000 | Weisz ............... G06F 17/30569 |

(Continued)

*Primary Examiner* — Kenneth R Coulter

(57) ABSTRACT

Methods and systems provide secure data transmission from a mobile device to a central computer system over a communication network. The method includes executing a first computer program in the mobile device and allocating by the first computer program a volatile memory space in the mobile device for a defined session. The method includes storing data in the allocated volatile memory space. The method includes transmitting the stored data to the central computer using a secure transmission protocol over the communication network. The method includes de-allocating by the first computer program the volatile memory space at the termination of the session. The de-allocation erases the transmitted data from the volatile memory space.

30 Claims, 2 Drawing Sheets

(56) References Cited

U.S. PATENT DOCUMENTS

| | | | |
|---|---|---|---|
| 6,237,079 B1 | 5/2001 | Stoney | |
| 7,430,671 B2 * | 9/2008 | Graves | H04L 63/0428 713/165 |
| 8,166,210 B2 | 4/2012 | Aoyama | |
| 8,316,460 B1 | 11/2012 | Wang et al. | |
| 2003/0100373 A1 * | 5/2003 | Fujimoto | G07C 9/00103 463/42 |
| 2003/0154398 A1 | 8/2003 | Eaton et al. | |
| 2003/0226006 A1 | 12/2003 | Ballard | |
| 2004/0221788 A1 | 2/2004 | Shizukuishi | |
| 2004/0162831 A1 | 8/2004 | Patterson | |
| 2005/0223222 A1 * | 10/2005 | Graves | H04L 63/0428 713/165 |
| 2009/0230179 A1 | 9/2009 | Livolsi et al. | |
| 2011/0223970 A1 | 9/2011 | Mori et al. | |
| 2015/0015911 A1 | 1/2015 | Shimizu | |
| 2015/0028578 A1 | 1/2015 | Pawlik et al. | |
| 2016/0037057 A1 * | 2/2016 | Westin | H04N 5/23222 348/207.1 |
| 2016/0103964 A1 * | 4/2016 | Osorio | G06F 19/322 705/3 |
| 2016/0104000 A1 * | 4/2016 | Osorio | G06F 19/322 726/26 |

* cited by examiner

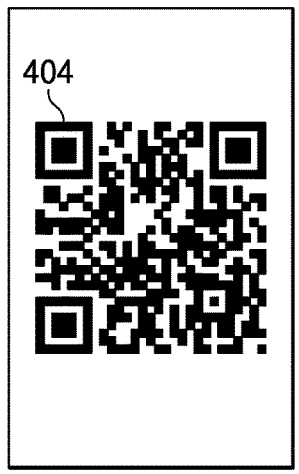
FIG. 4
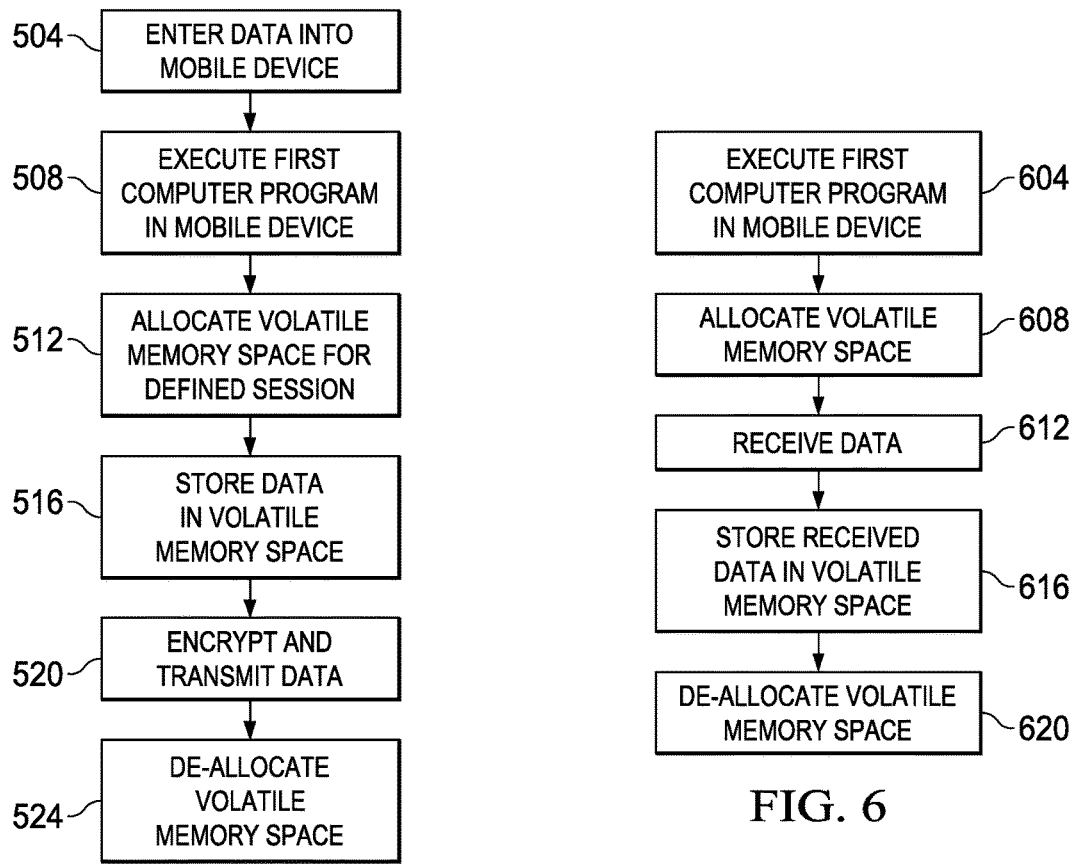
FIG. 5
FIG. 6

METHODS AND SYSTEMS FOR SECURE TRANSMISSION AND RECEPTION OF DATA BETWEEN A MOBILE DEVICE AND A CENTRAL COMPUTER SYSTEM

CROSS-REFERENCE TO RELATED APPLICATION

This application claims the benefit of U.S. Provisional Application Ser. No. 62/062,601, filed by Osorio, et al., on Oct. 10, 2014, entitled "Multi-feature Mobile Software Application that Generate [sic.] a Secure Environment to Capture Data under a HIPAA/Hitech Complaint [sic.] Protocol," commonly assigned with this application and incorporated herein by reference.

TECHNICAL FIELD

The disclosure relates to methods and systems for secure transmission and reception of data between a mobile device and a central computer system over a communication network.

BACKGROUND

The Health Insurance Portability and Accountability Act (HIPAA) requires healthcare providers (e.g., physicians), hospitals, health insurance companies and other businesses associated with the healthcare industry that receive patient health information (PHI) to implement control of access to computer systems and networks that store PHI. HIPAA requires that computer systems that store PHI are protected from intrusion. Also, HIPAA requires any communication containing PHI transmitted electronically over open networks is encrypted to prevent unauthorized interception.

Existing systems and methods generally do not allow mobile devices to securely acquire, transmit or receive data which may contain PHI.

SUMMARY

Various disclosed embodiments are directed to methods and systems for secure data transmission from a mobile device to a central computer over a communication network. The communication network may include a wireless network, a wired network and/or the Internet.

The method includes executing a first computer program in the mobile device and allocating by the first computer program a volatile memory space in the mobile device for a defined session. The method includes storing data in the allocated volatile memory space. A user may enter the data into the mobile device using a key pad or the data may be scanned in by an optical scanner.

The method includes transmitting the stored data to the central computer using a secure transmission protocol over the communication network. The method includes de-allocating by the first computer program the volatile memory space at the termination of the session. The de-allocation erases the transmitted data from the volatile memory space. Thus, the data is not persistently retained in the mobile device.

According to disclosed embodiments, access to the allocated volatile memory space during the session is restricted to only the first computer program. Thus, all other computer programs in the mobile device are prevented access to the allocated volatile memory space during the session.

According to disclosed embodiments, a method for secure data reception by a mobile device from a central computer over a communication network includes executing a first computer program in the mobile device and allocating by the first computer program a volatile memory space in the mobile device for a defined session. The method includes receiving data by the mobile device using a secure transmission protocol over the communication network. The method includes storing the received data in the allocated volatile memory space. The method includes de-allocating the volatile memory space at the termination of the session. The de-allocation erases the received data from the volatile memory space.

The foregoing has outlined rather broadly the features and technical advantages of the present disclosure so that those skilled in the art may better understand the detailed description that follows. Additional features and advantages of the disclosure will be described hereinafter that form the subject of the claims. Those skilled in the art will appreciate that they may readily use the conception and the specific embodiment disclosed as a basis for modifying or designing other structures for carrying out the same purposes of the present disclosure. Those skilled in the art will also realize that such equivalent constructions do not depart from the spirit and scope of the disclosure in its broadest form.

Before undertaking the DETAILED DESCRIPTION below, it may be advantageous to set forth definitions of certain words or phrases used throughout this patent document: the terms "include" and "comprise," as well as derivatives thereof, mean inclusion without limitation; the term "or" is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, whether such a device is implemented in hardware, firmware, software or some combination of at least two of the same. It should be noted that the functionality associated with any particular controller may be centralized or distributed, whether locally or remotely. Definitions for certain words and phrases are provided throughout this patent document, and those of ordinary skill in the art will understand that such definitions apply in many, if not most, instances to prior as well as future uses of such defined words and phrases. While some terms may include a wide variety of embodiments, the appended claims may expressly limit these terms to specific embodiments.

BRIEF DESCRIPTION

Reference is now made to the following descriptions taken in conjunction with the accompanying drawings, in which:

FIG. 4 shows an acquired image displayed on a mobile device;

FIG. 5 is a flow diagram of the method according to disclosed embodiments; and

FIG. 6 is a flow diagram of the method according to other disclosed embodiments.

DETAILED DESCRIPTION

FIGS. 1-6, discussed below, and the various embodiments used to describe the principles of the present disclosure are by way of illustration only and should not be construed in any way to limit the scope of the disclosure. Those skilled in the art will recognize that the principles of the disclosure may be implemented in any suitably arranged device or a system. The numerous innovative teachings of the present disclosure will be described with reference to exemplary non-limiting embodiments.

Various disclosed embodiments provide methods and systems for secure data communication between a mobile device and a central computer system. The mobile device is configured to transmit and receive data securely over a communication network which may, for example, include a wireless network, a wired network, and/or a wide area network (e.g., Internet). The central computer system may be a server (e.g., application server, database server) a desktop computer, a central processor or any other type of data processing system. The mobile device and the central computer system may communicate using a secure transmission protocol (STP).

According to disclosed embodiments, an application executable on a mobile communication device allows secure transmission and reception of data in compliance with Health Insurance Portability and Accountability Act (HIPAA). Healthcare providers may implement the disclosed embodiments to securely transmit and receive data containing patient health information (PHI). For example, healthcare providers may implement the disclosed embodiments to transmit data to health insurance companies in order to receive reimbursement for services provided or to receive pre-approval for services. Medical laboratories may implement the disclosed embodiments to transmit data containing laboratory reports to patients or other healthcare providers.

Figure 1:
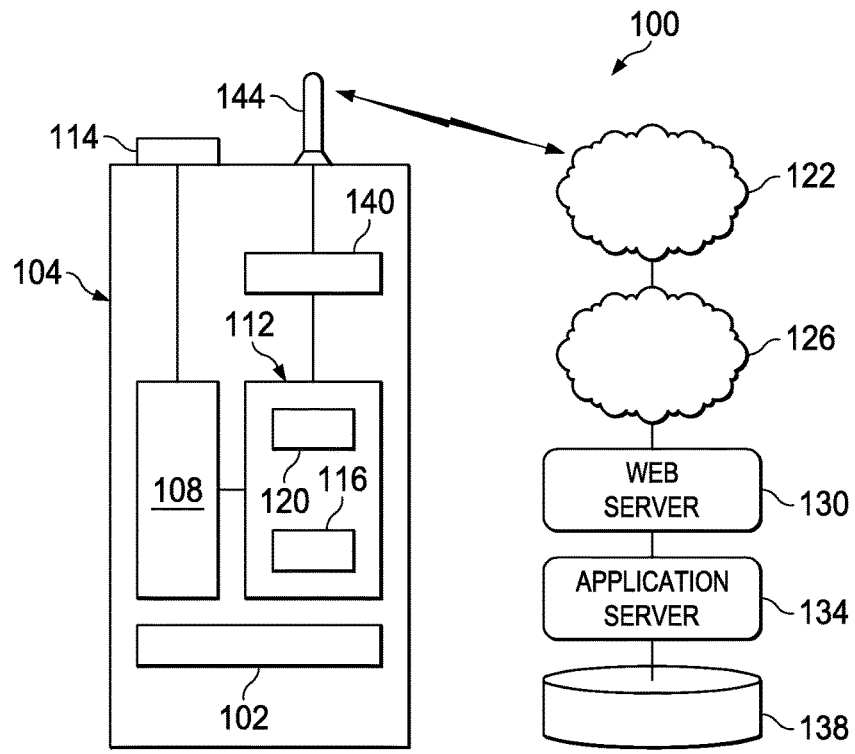
FIG. 1 is a schematic block diagram of a communication system in which embodiments of the disclosure can be implemented.

FIG. 1 is a schematic block diagram of a communication system 100 in which embodiments of the disclosure can be implemented. The system 100 includes a mobile communication device 104 which may take the form of a mobile phone, a laptop computer, a tablet computer or the like. The mobile device 104 is configured to wirelessly communicate with other communication devices via a communication network 122. The network 122 may include a mobile cellular network such as a 3GPP network or other CDMA/GSM network. The network 122 may be linked to another network 126 such as a wired network and/or the Internet 126.

The system 100 includes a central computer system. The central computer system may include a web server 130 and an application server 134. The central computer system may be connected to the Internet 126.

The mobile device 104 may communicate with the central computer system, i.e., the web server 130 and the application server 134, over the networks 122 and 126. For example, the mobile device 104 may retrieve one or more web pages from the web server 130 and may access one or more applications from the application server 134.

The mobile device 104 includes a processor 108 connected to a memory 112. The processor 108 may be of the type generally used in mobile devices such as those manufactured by Intel Corporation or ARM Holdings.

According to disclosed embodiments, the memory 112 comprises a non-volatile memory 116 and a volatile memory 120. In the non-volatile memory 116, any data stored is persistently retained even after electrical power is removed from the non-volatile memory 116. Thus, any data stored in the non-volatile memory 116 is not erased following removal of electrical power. In contrast, any data stored in the volatile memory 120 is erased, and thus lost, after electrical power is removed from the volatile memory 120. Thus, any data stored in the volatile memory 120 is not persistently retained after removal of electrical power.

The mobile device 104 includes a keypad 102. A user may enter data using the keypad 102. The mobile device 104 also includes a digital camera and/or an optical scanner 114 configured to scan in or acquire images. The scanned or acquired images are stored in the memory 112. The mobile device 104 also includes a transceiver 140 coupled to an antenna 144. The transceiver 140 and the antenna 144 allow the mobile device 104 to wirelessly transmit and receive data over a wireless network such as the network 122.

Figure 2:
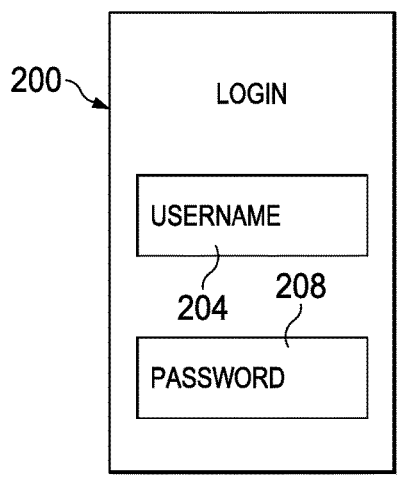
FIG. 2 illustrates an application executable on the mobile device according to disclosed embodiments.

According to disclosed embodiments, an application executable on a mobile communication device allows secure transmission and reception of data in compliance with HIPAA. FIG. 2 illustrates an exemplary application 200 executable on the mobile device 104. The application 200 is a computer program which may reside locally in the mobile device 104. The application 200 may be downloaded from the application server 134. Alternatively, the mobile device 104 may access the application 200 from the application server 134.

Figure 3:
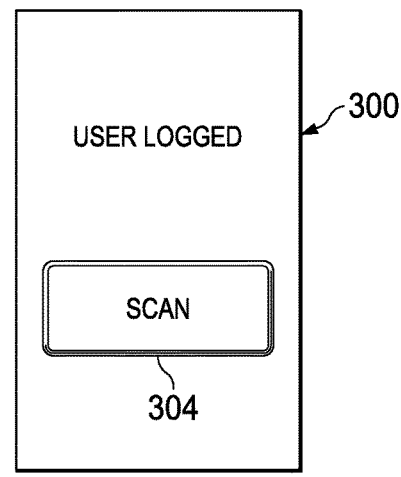
FIG. 3 illustrates the application with a data acquisition/image capture button.

The application 200 provides a username 204 field and a password 208 field displayed on the mobile device 104. A user can login by entering a username and a password. Upon successful login a connection is established with a secure server such as the server 130 and the server 134 over the networks 122 and 126. Once the user is logged on, a web page 300 is displayed which has an image capture button 304 as shown in FIG. 3. The user can press the image capture button 304 to activate the optical scanner and/or digital camera 114 of the mobile device 104 to scan or acquire an image. FIG. 4 shows an acquired image 404 including a date and time stamp 408 which are displayed on the mobile device 104. As discussed before, a user may also enter data using the keypad 102.

According to disclosed embodiments, a volatile memory space in the volatile memory 120 is allocated by the processor 108 for a defined session and de-allocated at the termination of the session. The session is defined for a predetermined time period. According to disclosed embodiments, the volatile memory space may be allocated by marking portions of it as being allocated to the application 200 in a memory allocation table and de-allocated by marking those portions as unallocated at the termination of the session and perhaps also overwriting it. Alternatively, the volatile memory space may be allocated by applying electrical power to the volatile memory 120 and de-allocated by removing electrical power at the termination of the session. Volatile memory space that is temporarily allocated to an application is sometimes called "scratchpad" memory. In the context of certain mobile device operating systems commercially available from Apple Incorporated of Cupertino, Calif. (e.g., OS X®), such temporarily allocated volatile memory is called a "sandbox" and is designed to prevent applications from interfering with one another or the operating system, except as the operating system permits.

According to disclosed embodiments, the data (entered using the key pad or scanned in) is stored in the allocated volatile memory space. The volatile memory space may be a random access memory (RAM).

According to disclosed embodiments, access to the stored data is restricted or otherwise limited to the application 200 only. All other applications in the mobile device 104 are prevented from accessing or using the data.

The stored data is then encrypted and transmitted to a remote server using a secure transmission protocol. For example the data may be encrypted and transmitted to the application server 134 over the networks 122 and 126. In accordance with the secure transmission protocol, at the remote server the encrypted image is authenticated upon reception.

According to disclosed embodiments, after the termination of the session, the volatile memory space is de-allocated which causes the stored data to be erased from the volatile memory space. The volatile memory space is de-allocated by marking the volatile memory space as unallocated at the termination of the session and perhaps overwriting it. Consequently, the data is not persistently retained in the mobile device 104 after the termination of the session.

Thus, it will be appreciated that the disclosed embodiments provide secure transmission and reception of data in compliance with HIPAA. Since the data is erased from the volatile memory after the defined session, and thus not persistently retained by the mobile device 104, the data is protected from intrusion and misappropriation. Also, because the transmitted data is encrypted, they are prevented from unauthorized interception.

FIG. 5 is a flow diagram of the method according to disclosed embodiments. In block 504, data is entered into a mobile device. The data may, for example, be entered using a key pad or may be scanned in by an optical scanner. The data may include protected healthcare information of a patient.

In block 508, a first computer program is executed in the mobile device. The first computer program may reside locally in the mobile device. Alternatively, the first computer program may be downloaded by the mobile device from an external computer.

In block 512, the first computer program allocates a volatile memory space in the mobile device for a defined session. The volatile memory space may be a random access memory allocated for a predetermined time period by marking it as allocated or applying electrical power to it.

In block 516, the data is stored in the allocated volatile memory space. According to disclosed embodiments, access to the allocated volatile memory space during the session is restricted or limited to only the first computer program. All other computer programs in the mobile device are prevented from accessing the allocated volatile memory space during the session.

In block 520, the stored data is encrypted, and the encrypted data is transmitted over a communication network using a secure transmission protocol to a central computer. The communication network may, for example, include a wireless network, a wired network, and/or the Internet. Upon reception at the central computer, the data is authenticated.

In block 524, the volatile memory space is de-allocated by the first computer program at the termination of the session. The de-allocation of the volatile memory space erases the transmitted data from the volatile memory space. Thus, the data is not persistently retained by the mobile device.

According to disclosed embodiments, the volatile memory space may be de-allocated by marking the volatile memory space as unallocated upon the termination. The volatile memory space is a random access memory (RAM).

FIG. 6 is a flow diagram of a method according to other disclosed embodiments. In block 604, a first computer program is executed in a mobile device. In block 608, a volatile memory space is allocated by the first computer program. According to disclosed embodiments, the volatile memory space is allocated for a defined session.

In block 612, data is received by the mobile device using a secure transmission protocol over a communication network. The communication network may, for example, include a wireless network and/or the Internet.

In block 616, the received data is stored in the allocated volatile memory space. In block 620, the volatile memory space is de-allocated. According to disclosed embodiments, the volatile memory space is de-allocated at the termination of the session. The de-allocation of the volatile memory space erases the received data from the volatile memory space.

According to disclosed embodiments, a non-transitory computer-readable medium is encoded with first computer-executable instructions for secure data transmission from a mobile device to a central computer over a communication network. The first computer-executable instructions when executed cause at least one data processing system to: allocate a volatile memory space in the mobile device for a defined session; store data in the allocated volatile memory space; transmit the stored data to the central computer using a secure transmission protocol over the communication network; de-allocate the volatile memory space at the termination of the session. The de-allocation erases the transmitted data from the volatile memory space.

Those skilled in the art will recognize that, for simplicity and clarity, the full structure and operation of all systems suitable for use with the present disclosure is not being depicted or described herein. Instead, only so much of a system as is unique to the present disclosure or necessary for an understanding of the present disclosure is depicted and described. The remainder of the construction and operation of the disclosed systems may conform to any of the various current implementations and practices known in the art.

Of course, those of skill in the art will recognize that, unless specifically indicated or required by the sequence of operations, certain steps in the processes described above may be omitted, performed concurrently or sequentially, or performed in a different order. Further, no component, element, or process should be considered essential to any specific claimed embodiment, and each of the components, elements, or processes can be combined in still other embodiments.

It is important to note that while the disclosure includes a description in the context of a fully functional system, those skilled in the art will appreciate that at least portions of the mechanism of the present disclosure are capable of being distributed in the form of instructions contained within a machine-usable, computer-usable, or computer-readable medium in any of a variety of forms, and that the present disclosure applies equally regardless of the particular type of instruction or signal bearing medium or storage medium utilized to actually carry out the distribution. Examples of machine usable/readable or computer usable/readable mediums include: nonvolatile, hard-coded type mediums such as read only memories (ROMs) or erasable, electrically programmable read only memories (EEPROMs), and user-recordable type mediums such as floppy disks, hard disk drives and compact disk read only memories (CD-ROMs) or digital versatile disks (DVDs).

Although an exemplary embodiment of the present disclosure has been described in detail, those skilled in the art will understand that various changes, substitutions, variations, and improvements disclosed herein may be made without departing from the spirit and scope of the disclosure in its broadest form.

None of the description in the present application should be read as implying that any particular element, step, or function is an essential element which must be included in the claim scope: the scope of patented subject matter is defined only by the allowed claims. Moreover, none of these claims are intended to invoke paragraph six of 35 USC § 112 unless the exact words "means for" are followed by a participle.

What is claimed is:

1. A method for secure data transmission from a mobile device to a central computer over a communication network, comprising:
   executing a first computer program in the mobile device;
   allocating by the first computer program a volatile memory space in the mobile device for a defined session;
   storing data in the allocated volatile memory space;
   transmitting the stored data in the mobile device to the central computer using a secure transmission protocol over the communication network; and
   de-allocating, by the first computer program in the mobile device, the volatile memory space at the termination of the session,
   wherein the de-allocation erases the transmitted data from the volatile memory space and causes the transmitted data to not be persistently retained in the mobile device, wherein the non-persistent retention of the transmitted data is in compliance with the Health Insurance Portability and Accountability Act (HIPAA).

2. The method of claim 1, further comprising entering the data into the mobile device using a keypad.

3. The method of claim 1, further comprising acquiring the data using an optical scanner in the mobile device.

4. The method of claim 1, wherein access to the allocated volatile memory space during the session is restricted to only the first computer program, and wherein all other computer programs in the mobile device are prevented access to the allocated volatile memory space during the session.

5. The method of claim 1, wherein the data cannot be accessed by any other computer programs in the mobile device except by the first computer program.

6. The method of claim 1, wherein the first computer program is downloaded from the central computer.

7. The method of claim 1, wherein the secure transmission protocol encrypts the data prior to the transmission.

8. The method of claim 1, wherein the volatile memory space is de-allocated by marking the volatile memory space as unallocated upon the termination.

9. The method of claim 1, wherein the volatile memory space is a random access memory (RAM).

10. The method of claim 1, wherein the secure transmission protocol authenticates the data upon reception by the central computer.

11. The method of claim 1, wherein the session is defined for a predetermined time period.

12. The method of claim 1, wherein the communication network comprises a wireless network.

13. The method of claim 1, wherein the communication network comprises the Internet.

14. A method for secure data reception by a mobile device from a central computer over a communication network, comprising:
   executing a first computer program in the mobile device;
   allocating by the first computer program a volatile memory space in the mobile device for a defined session;
   receiving data by the mobile device using a secure transmission protocol over the communication network;
   storing the received data in the allocated volatile memory space in the mobile device; and
   de-allocating the volatile memory space at the termination of the session,
   wherein the de-allocation erases the received data from the volatile memory space in the mobile device,
   wherein erasure of data is in compliance with the Health Insurance Portability and Accountability Act (HIPAA.)

15. The method of claim 14, wherein the de-allocation of the volatile memory space causes the received data to not be persistently retained in the mobile device.

16. The method of claim 14, wherein access to the allocated volatile memory space during the session is restricted to only the first computer program, and wherein all other computer programs in the mobile device are prevented access to the allocated volatile memory space during the session.

17. The method of claim 14, wherein the data cannot be accessed by any other computer programs in the mobile device except by the first computer program.

18. The method of claim 14, wherein the first computer program is downloaded from the central computer.

19. The method of claim 14, wherein the secure transmission protocol encrypts the data prior to transmission from the central processor.

20. The method of claim 14, wherein the volatile memory space is de-allocated by marking the volatile memory space as unallocated upon the termination.

21. The method of claim 14, wherein the volatile memory space is a random access memory (RAM).

22. The method of claim 14, wherein the secure transmission protocol authenticates the data upon reception by the mobile device.

23. The method of claim 14, wherein the session is defined for a predetermined time period.

24. The method of claim 14, wherein the communication network comprises a wireless network.

25. The method of claim 14, wherein the communication network comprises the Internet.

26. A non-transitory computer-readable medium encoded with first computer-executable instructions for secure data transmission from a mobile device to a central computer over a communication network, wherein the first computer-executable instructions when executed cause at least one data processing system to:
   allocate a volatile memory space in the mobile device for a defined session;
   store data in the allocated volatile memory space;
   transmit the stored data in the mobile device to the central computer using a secure transmission protocol over the communication network; and
   de-allocate the volatile memory space in the mobile device at the termination of the session,
   wherein the de-allocation erases the transmitted data from the volatile memory space and causes the transmitted data to not be persistently retained in the mobile device, wherein the non-persistent retention of the transmitted data is in compliance with the Health Insurance Portability and Accountability Act (HIPAA).

27. The non-transitory computer-readable medium of claim 26, wherein the data is entered into the mobile device using a keypad.

28. The non-transitory computer-readable medium of claim 26, wherein the data is acquired by an optical scanner in the mobile device.

29. The non-transitory computer-readable medium of claim 26, wherein the data cannot be accessed by any other computer programs in the mobile device except by the first computer-executable instructions.

30. The non-transitory computer-readable medium of claim 26, wherein the first computer readable instructions are downloaded from the central computer.

* * * * *

UNITED STATES PATENT AND TRADEMARK OFFICE
CERTIFICATE OF CORRECTION

PATENT NO. : 10,388,408 B2
APPLICATION NO. : 14/879248
DATED : August 20, 2019
INVENTOR(S) : Federico Osorio and Andres Gutierrez Ovalles Page 1 of 1

It is certified that error appears in the above-identified patent and that said Letters Patent is hereby corrected as shown below:

In the Specification

In Column 1, Line 30, after --receive-- delete "patient" and insert --protected--

Signed and Sealed this
Tenth Day of November, 2020

Andrei Iancu
*Director of the United States Patent and Trademark Office*